(12) United States Patent
Mahgoub (10) Patent No.: US 12,023,277 B2
(45) Date of Patent: Jul. 2, 2024

(54) CONTACT LENS INSERTION SYSTEM

(71) Applicant: Augmented Vision Labs, Fort Collins, CO (US)

(72) Inventor: Fayiz Osman Mahgoub, Fort Collins, CO (US)

(73) Assignee: Augmented Vision Labs, LLC, Fort Collins, CO (US)

( * ) Notice: Subject to any disclaimer, the term of this patent is extended or adjusted under 35 U.S.C. 154(b) by 749 days.

(21) Appl. No.: 17/159,801

(22) Filed: Jan. 27, 2021

(65) Prior Publication Data

US 2021/0236337 A1  Aug. 5, 2021

Related U.S. Application Data

(60) Provisional application No. 62/968,128, filed on Jan. 30, 2020.

(51) Int. Cl.
*A61F 9/00* (2006.01)
*G02C 7/04* (2006.01)

(52) U.S. Cl.
CPC .............. *A61F 9/0061* (2013.01); *G02C 7/04* (2013.01)

(58) Field of Classification Search
CPC ................................. A61F 9/0061; G02C 7/04
USPC .......................................................... 294/1.2
See application file for complete search history.

(56) References Cited

U.S. PATENT DOCUMENTS

| | | | | |
|---|---|---|---|---|
| 3,304,113 A | * | 2/1967 | Hutchison | A61F 9/0061 351/159.02 |
| 4,093,291 A | * | 6/1978 | Schurgin | A61F 9/0061 294/1.2 |
| 4,378,126 A | * | 3/1983 | Procenko | A61F 9/0061 294/1.2 |
| 7,163,245 B2 | | 1/2007 | Wallock et al. | |
| 7,193,622 B2 | * | 3/2007 | Sklovsky | G09G 5/02 345/204 |
| 8,015,987 B2 | * | 9/2011 | Zakutin | A61L 12/02 134/901 |
| 8,444,193 B2 | * | 5/2013 | Finck | B65G 7/12 294/187 |
| D791,858 S | * | 7/2017 | Tillmann | D16/331 |
| 10,182,938 B2 | * | 1/2019 | Hopper | A61F 9/00 |
| D898,814 S | * | 10/2020 | Tillmann | D16/331 |
| 11,376,156 B1 | | 7/2022 | Morarie | |
| 2019/0216644 A1 | * | 7/2019 | Hershoff | B25J 15/0683 |
| 2023/0094850 A1 | * | 3/2023 | Hunter | A61F 9/0061 606/107 |

* cited by examiner

*Primary Examiner* — Paul T Chin
(74) *Attorney, Agent, or Firm* — DeWitt LLP (57) ABSTRACT

A contact lens application aid including a lens holder dock structured and dimensioned to receive a lens holder and a light unit optically coupled to the lens holder dock and illuminating the lens holder dock. The contact lens application aid further includes a first supporting member extending downwardly away from the light unit whereby the light unit and lens holder are supported at a desired height above a horizontal work surface. The first supporting member is supported on a surface engaging supporting base coupled to the supporting member. The contact lens application aid enables a user to keep both hands free to manipulate eyelids while applying a contact lens to the eye.

17 Claims, 10 Drawing Sheets

CONTACT LENS INSERTION SYSTEM

CROSS-REFERENCE TO RELATED APPLICATION

This application claims the benefit of U.S. provisional patent application 62/968,128 filed Jan. 30, 2020 entitled "Contact Lens Insertion System" the contents of which are incorporated herein in their entirety by reference.

TECHNICAL FIELD

Embodiments of the invention relate to the field of contact lenses. More particularly embodiments of the invention relate to appliances and aids to assist in contact lens insertion or contact lens application.

BACKGROUND

Contact lens insertion can be a challenging process for many contact lens wearers. Lens insertion can be complicated by factors such as the human blink reflex which is triggered by objects being placed near or on the eye. Other factors that can impede contact lens application include a narrow interpalpebral aperture (a narrow opening between the eyelids) or difficulty with fine motor control of the hands or fingers (possibly associated with conditions such as Parkinson's disease, arthritis, or stroke). Lens insertion can be particularly challenging for the application of specialty lenses (such as scleral lenses and hybrid lenses) because these lenses include a rigid gas permeable material for at least part of the lens structure. The rigid or semi-rigid nature of these lenses requires that concave surface of the lens to be filled with saline solution or other contact lens solution to mitigate air bubbles from becoming trapped between the lens and the eye of the wearer. Air bubbles may contribute to poor vision with lenses in place and wearer discomfort. Wearers often find it challenging to prevent the saline solution from spilling during lens insertion, leading to air bubbles between the lens and the eye. The presence of air bubbles often requires the lens to be removed and reinserted.

Scleral and hybrid contact lenses can also be more challenging to insert than soft lenses because these lenses are larger in diameter than other lenses. Accordingly, the opening between the eyelids must be made wider than the diameter of the lens in order for the lens to be inserted which can be a challenge for wearers who have a naturally narrow interpalpebral aperture (a narrow opening between the eyelids).

A variety of assistive devices exist to aid people with the application of contact lenses to the eye. Unfortunately, these devices are often of limited effectiveness. Thus, there is still room for improvement in this field.

SUMMARY

An assistive contact lens application device according to example embodiments of the invention addresses many of these challenges that are associated with contact lens insertion. The device allows for hands-free lens stabilization by incorporating a universal dock to which a variety of lens holders can be connected.

By docking the lens holder to this device, the user is freed from needing to hold the lens holder in their hand during lens application or insertion which allows the user to have two hands free to hold their eyelids open. This helps the user to control the human blink reflex more effectively because they have more fingers free to control the eyelids and can place their hand in the best possible orientation to immobilize the eyelids than if they were trying to simultaneously hold the lens holder and spread their eyelids open.

The lens stabilization provided by the universal lens holder dock also helps reduce spilling of the lens insertion solution because it keeps the lens stationery and level with the ground. Without this feature it's more likely for users to spill the saline lens insertion solution by inadvertently tilting the lens holder as they attempt to spread and hold their eyelids open. By reducing spillage of the saline solution, embodiments of the invention reduce the likelihood of air bubbles getting trapped between the lens and the surface of the eye.

According to another example embodiment of the invention, the device has an adjustable height which allows the user to utilize it while sitting or standing and allows them to position the lens at the most comfortable height for insertion.

Another example embodiment of the device features an LED light source or other light source that enables the user to more easily align their eye with the center of the lens during insertion. The light source may include the use of a glow-in-the-dark material, containing for example zinc sulfide, strontium aluminate or another material that behaves phosphorescently. Such a luminescent material can be incorporated for example into a lens holder dock or a lens holder plug and can be utilized to provide a light target for the user passively without the incorporation of electronic illumination components or for use in conjunction with actively illuminated components to conserve battery life or to act as a backup in case of insufficient battery power. Illumination of the lens holder is particularly helpful for patients who have a significant visual impairment and find it difficult to see the lens (which is relatively transparent in color) during insertion.

Device Components

On/Off Mechanism

According to an example embodiment, the light source of the device can be turned on and off via a twist mechanism, but is not limited to this type of mechanism. Alternate mechanisms include a push button mechanism, a rotary switch that may or may not have a dimming feature, a toggle switch which incorporates a lever that can be actuated back and forth or a combination of any of the previously mentioned mechanisms.

The light source for this device may include a light emitting diode but, this should not be considered limiting. The color of the emitted light is white light, but is not limited to this color. Other colors of illumination may be helpful depending upon the degree and type of visual impairment experienced by the user.

Example embodiments of the device of the invention can be used with a lens holder called the Vented Scleral Cup which is manufactured by DMV corporation, but the device is not limited to this particular lens holder and may be utilized with a variety of other contact lens holding structures.

According to a further example embodiment, the light for source for the device can utilize LR44 batteries. According to this example embodiment a light unit upper segment threads into the light unit lower segment and in the process compresses the battery contact of the light emitting diode against the batteries in the device. This completes the circuit and causes the LED to emit light. Unthreading the light unit upper segment from the light unit lower segment opens the circuit and causes the LED to extinguish.

Lens Holder Dock

Example embodiments of the invention include a lens holder dock. The shape and size of the lens holder dock can have different dimensions to allow it to accommodate a variety of lens holders of various sizes and shapes. The lens holder according to an example embodiment is attached to the light unit of the device, for example, via a screw or other fastener mechanism. Alternative attachments may include adhesives, other fasteners, rivets, magnets, screw, slot or latch mechanisms. The lens holder docket can also be integrally formed with the light unit or may be independent of a light unit and utilize without a light unit. Accordingly, in some embodiments the lens holder dock may be secured to the base lever or to a telescoping or nonadjustable arm.

Battery

Generally, a battery provides a power source for the light source to facilitate portability. In an example embodiment, the battery used in this device is a rechargeable (also known as a secondary battery) lithium ion battery. However, the power source is not limited to this type of battery chemistry or recharging ability. Alternative battery types include, for example, disposable batteries (also known as a primary battery) such as AA, AAA, CR2032 and LR44. Example embodiments of the device may include one or multiple batteries and the batteries may have one or multiple cells. As an alternate to lithium ion battery, the device may incorporate one or more zinc-carbon batteries, alkaline-cell batteries, and mercury batteries. A combination of all the previously mentioned battery technologies may also be used. An external power source may be used as well. According to a further example embodiment, capacitors may be utilized for energy storage as an alternative to batteries.

Base

The base of the device, according to example embodiments, is used to stabilize the device. This base may incorporate a suction mechanism to adhere itself to the surface on which it is placed, but is not limited to this type of mechanism. Alternatively, the base may incorporate one or more legs that stabilize the device through having multiple contact points with the surface upon which it's placed. The base of the device may incorporate one or more telescoping segments to facilitate height adjustment of the device or it may have a fixed height. In the embodiments that incorporate legs as part of the base, the legs may be foldable or fixed in place. The base may incorporate several interchangeable attachment mechanisms. This includes, but is not limited to adhesives, fasteners, rivets, magnets and mechanisms including screw, slot or latch mechanisms. The light unit for this device is detachable from the base, but it is not limited to this configuration.

Attachment mechanisms used to join the base to the light unit include but are not limited to adhesives, fasteners, rivets, magnets, screw, slot or latches. Further example embodiments utilize a friction fit to reversibly or irreversibly couple the light unit to the base or to a telescoping arm. The light unit and base may also be in a joined configuration which may not require or may not allow the user to separate the light unit from the base under normal use conditions. The base may be made from plastic, metal or a combination of a variety of plastics and metals.

Light Unit Shape

The light unit may have a cylindrical shape, but is not limited to this shape. Alternative shapes include, triangular, rectangular or other polygon derived shapes.

Anti-Roll Mechanism

The device incorporates outgrowths (referred to as "anti-roll fins" in the included images) that mitigate the device rolling if placed on its side on a flat surface.

Battery Charging Mechanism

The version of the device that utilizes a rechargeable battery incorporates USB charging to replenish the battery, but is not limited to this method of battery charging. The USB port that is incorporated into the light unit is protected by a shroud that protects the charging connector from coming into contact with liquids used during lens insertion.

Height Adjustment Mechanism

A height adjustment mechanism allows the user to increase or decrease the height of the device as needed. This allows the user to have the lens stabilized at the height that they find most comfortable and allows the user the option of using the device while standing or sitting without the need of any additional accessories. An example embodiment utilizes a telescoping mechanism to achieve this, but is not limited to this type of mechanism. Alternatively, the device may be made with segments (which each can incorporate a telescoping functionality or may be fixed in length) that attach to one another to allow the height of the device from the stabilizing/attachment surface variable. The telescoping arm incorporated in the version of the device with height adjustment incorporates a dock for the light unit at a top end thereof which allows the USB connector to be joined to the telescoping arm.

Base Lever

The base lever is a component attached to the iteration of the device that contains a suction base. This component is used as a lever that engages suction within the suction base when it's pivoted from being horizontal to the attachment surface to being perpendicular to the attachment surface. In the version of the device with fixed height, the base lever also incorporates a coupler that allows the USB connector at the bottom of the light unit to slot into the base lever.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

Figure 1:
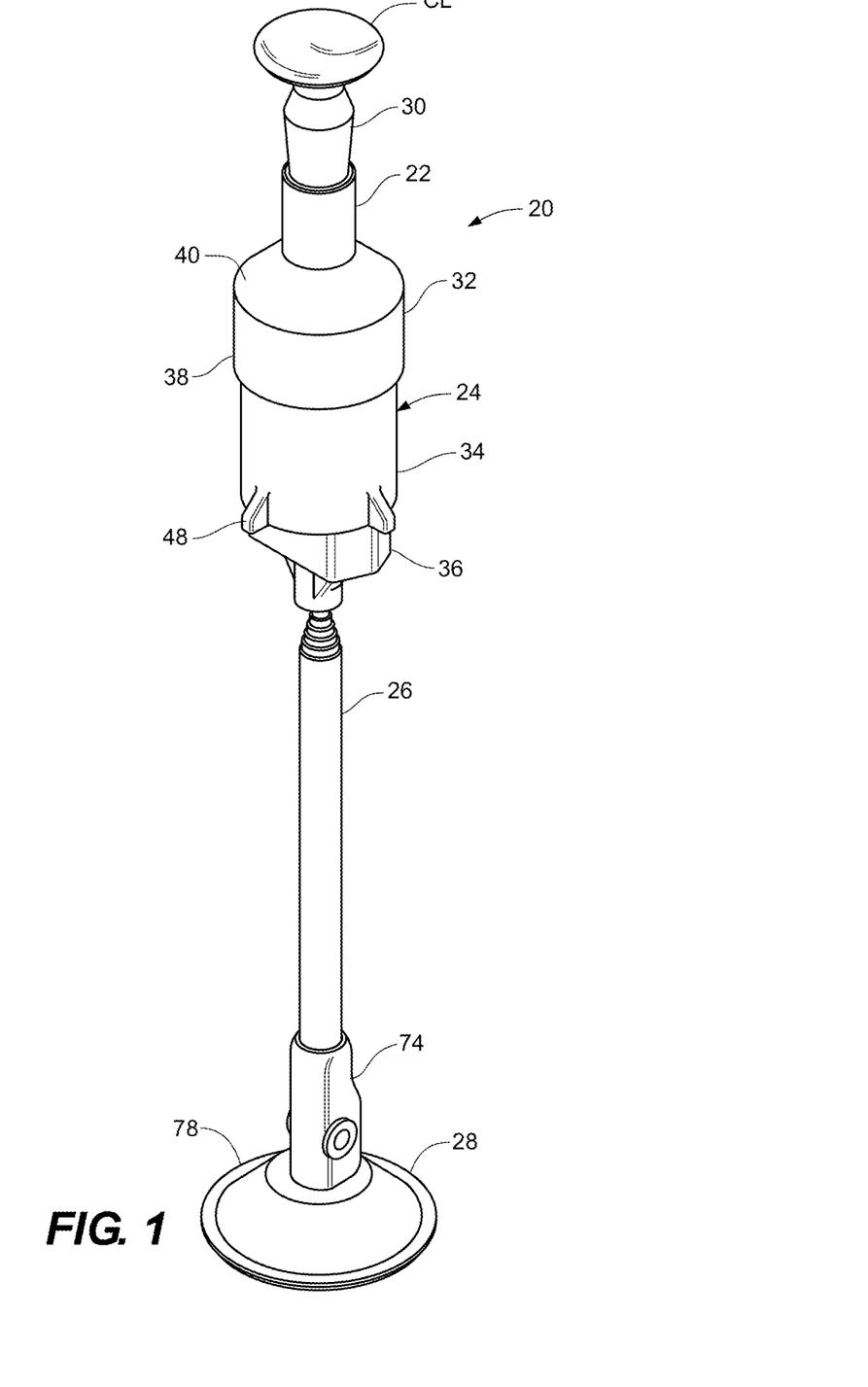
FIG. 1 is a perspective view of a contact lens application aid according to an example embodiment of the invention.
Figure 2:
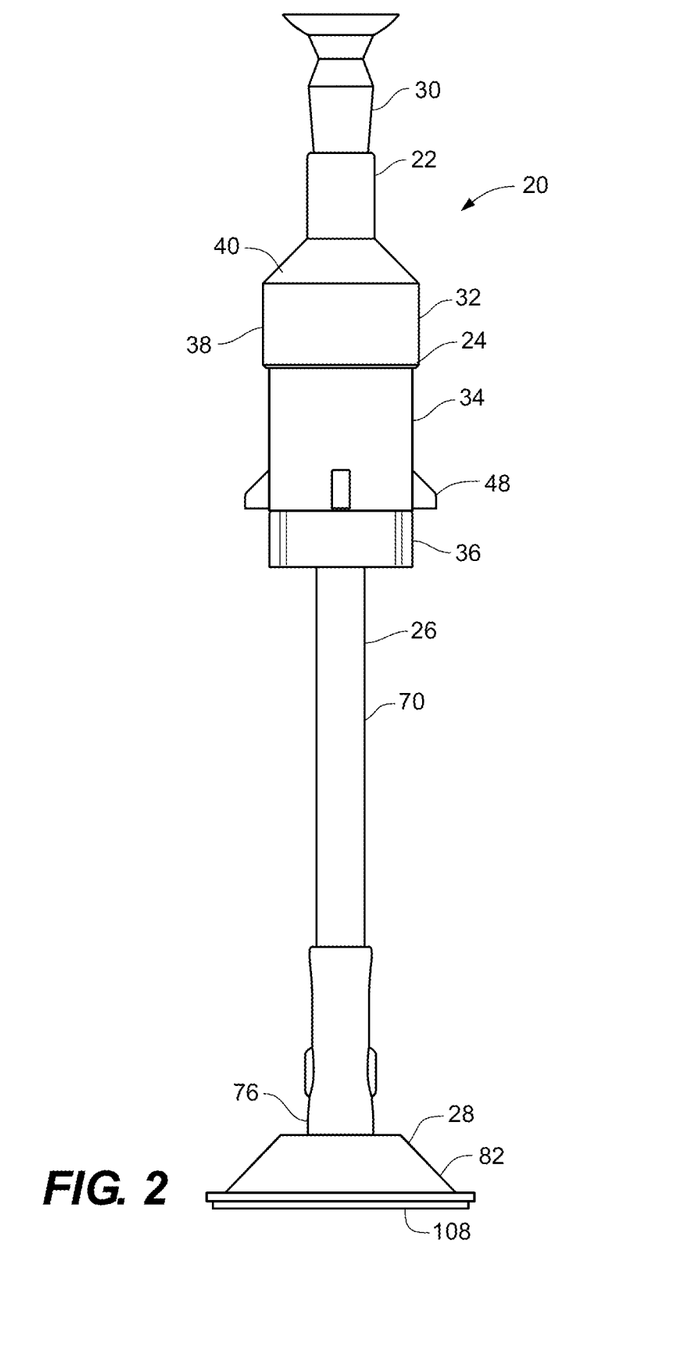
FIG. 2 is a perspective view of a contact lens application aid according to another example embodiment of the invention.
Figure 10:
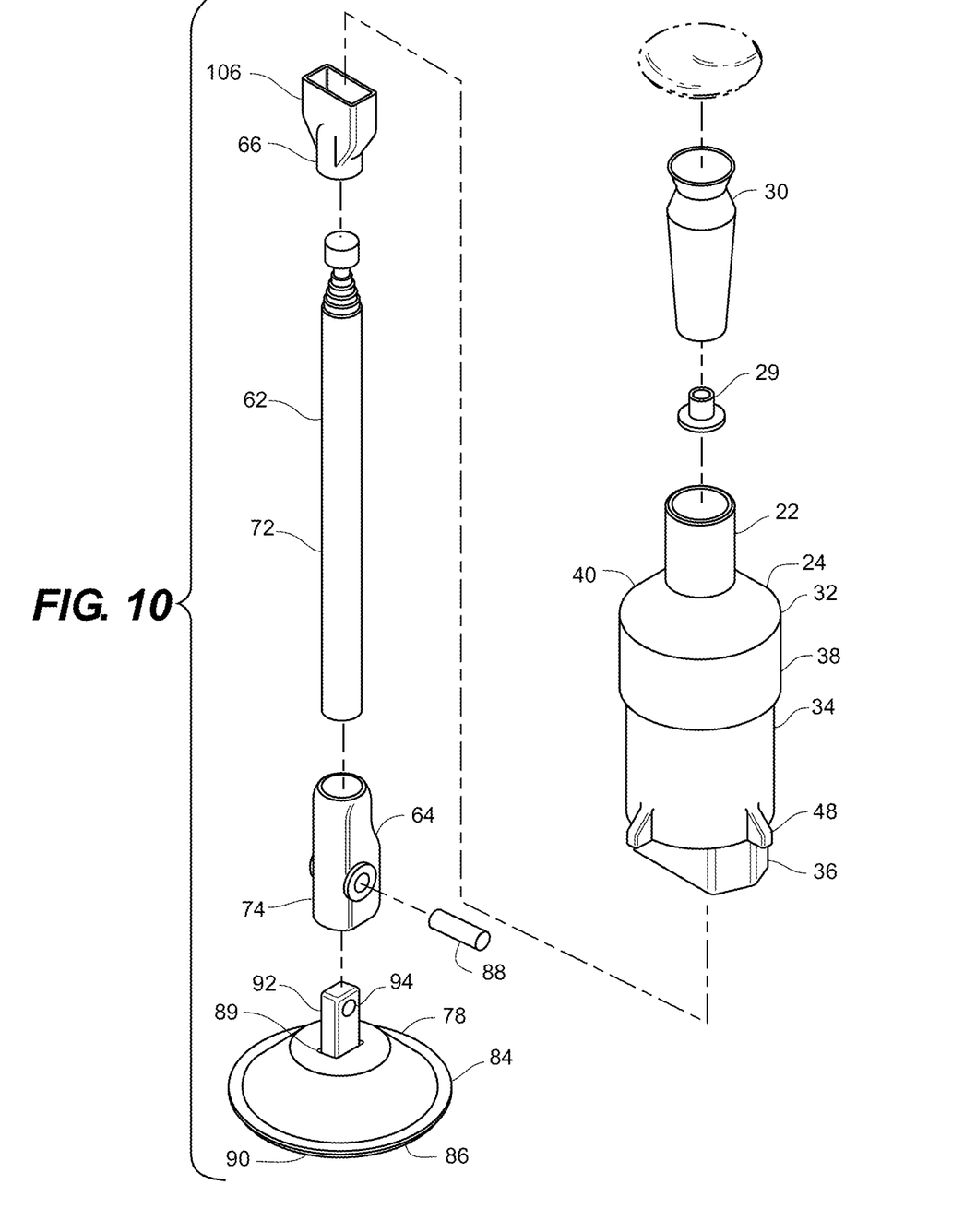
FIG. 10 is a partially exploded view of the contact lens application aid as depicted in FIG. 1.

Referring to FIGS. 1, 2 and 10 contact lens application aid 20 according to example embodiments of the invention generally includes lens holder dock 22, light unit 24, supporting member 26 and supporting base 28.

Lens holder dock 22 is adapted to receive lens holder plug 29 and lens holder 30 and, according to an example embodiment, may be formed of a transparent or translucent material. Material of lens holder dock 22 transmits light from light unit 24 to lens holder 30 via lens holder plug 29.

Figure 3:
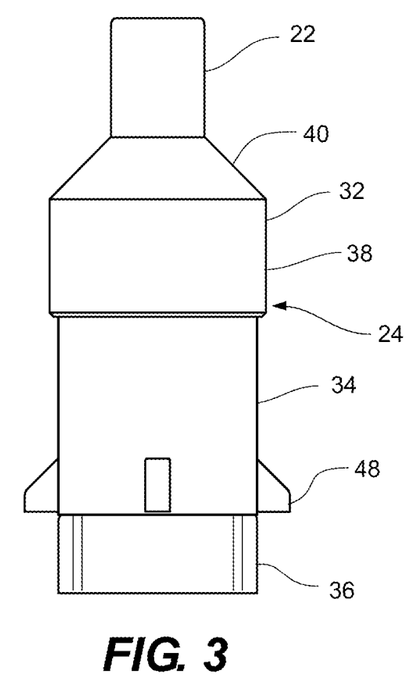
FIG. 3 is a perspective view of a lighting unit and lens holder Dock according to an example embodiment of the invention.
Figure 4:
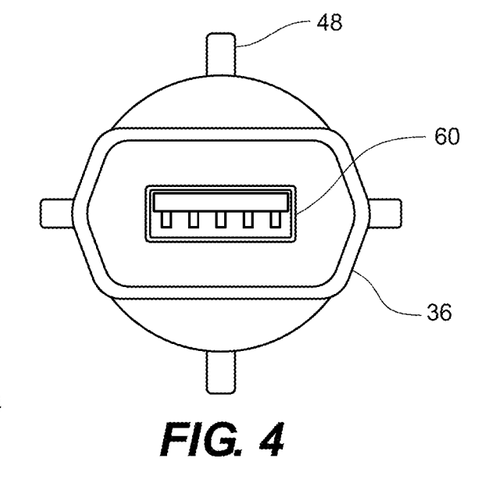
FIG. 4 is a bottom view of the lighting unit and lens holder Dock as depicted in FIG. 3.
Figure 5A:
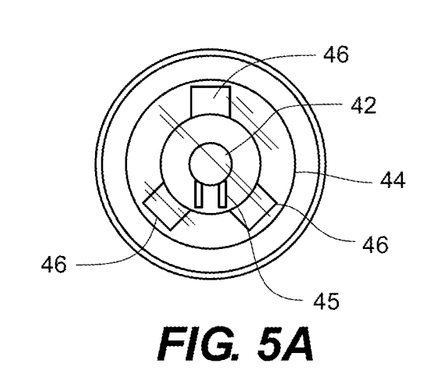
FIGS. 5A and 5B are partially disassembled views of the lighting unit as depicted in FIG. 3.
Figure 5B:
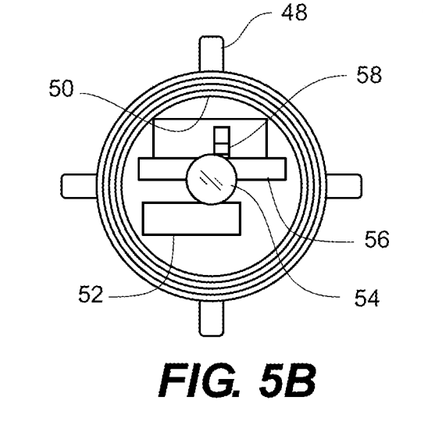

Referring particularly to FIGS. 3, 4 and 5, light unit 24 generally includes light unit upper segment 32, light unit lower segment 34 and charging port shroud 36.

Light unit upper segment 32, in the depicted embodiments, includes cylindrical portion 38 and frustoconical portion 40. Frustoconical portion 40 is coupled to lens holder dock 22 at one end thereof and to cylindrical portion 38 at another end thereof. Light unit upper segment 32 may be integrally formed with lens holder docked 22.

Referring particularly to FIG. 5A, internally, light unit upper segment 32 further includes focusing lens 42 supported by carrier 44. Carrier 44 may present switch actuating tabs 45 and be secured to light unit upper segment 32 for example by retaining tabs 46.

Light unit lower segment 34 is generally cylindrical in structure in the depicted embodiment and presents anti-roll fins 48. Four antiroll fins 48 are present in the depicted embodiment but a greater or lesser number may be present as well.

Referring particularly to FIG. 5B, Internally, light unit lower segment 34 presents upper segment retaining groove 50, rechargeable battery 52, light-emitting diode 54, printed circuit board 56 and switch 58. Rechargeable battery 52, light-emitting diode 54 printed circuit board 56 and switch 58 are electrically coupled appropriately to actuate and de-actuate light-emitting diode 54 as desired. Upper segment retaining groove 50 is structured to detachably couple light unit lower segment 34 to light unit upper segment 32.

Charging port shroud 36 extends downwardly from light unit lower segment 34 and surrounds charging port 60. In the depicted example embodiment charging port shroud 36 has the shape roughly of an irregular hexagon but this shape should not be considered limiting. In an example embodiment charging port 60 is a USB electrical coupler but this should not be considered limiting as other electrical couplers may be utilized. Any electrical coupler known to those skilled in the art can be utilized. Charging port shroud 36 may, for example, be formed integrally with light unit lower segment 34.

Figure 6:
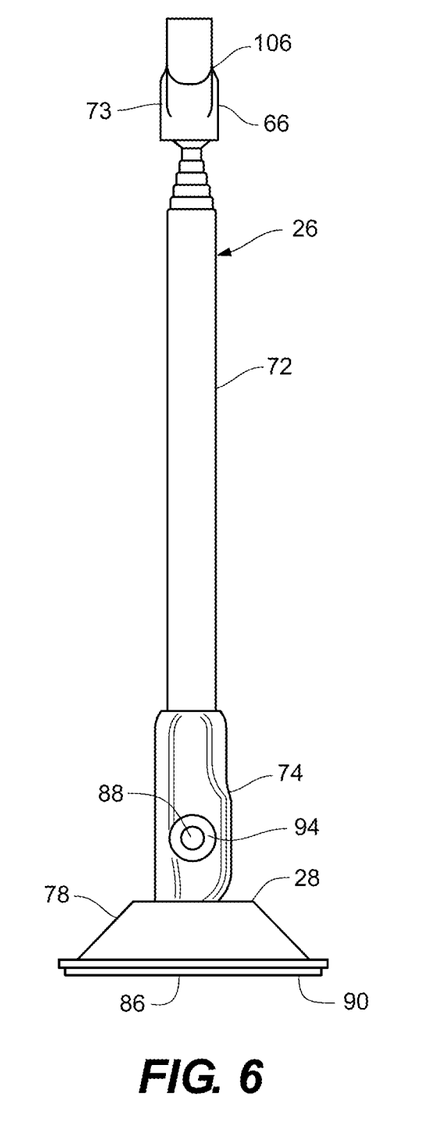
FIG. 6 is a perspective view of a suction base and telescoping arm according to an example embodiment of the invention.

Referring to FIGS. 1, 2 and 6, supporting member 26 generally includes supporting member body 62, base end 64 and coupling end 66. Base end 64 is structured and adapted to couple to supporting base 28. Coupling end 66 is structured and adapted to couple to light unit 24 for example at charging port shroud 36.

Supporting member body 62 may include fixed height supporting member 62 as depicted in FIG. 2 or adjustable height supporting member 64 as depicted in FIG. 1 for example. Adjustable height supporting member 64 may be embodied as a telescoping structure.

According to an example embodiment depicted in FIG. 6, coupling end 66 may include light unit dock 73. Light unit dock 73 is structured and adapted to be received into charging port shroud 36 and to engage charging port 60.

Base end 64 may include in different embodiments base lever 74 or base nut 76.

Figure 7:
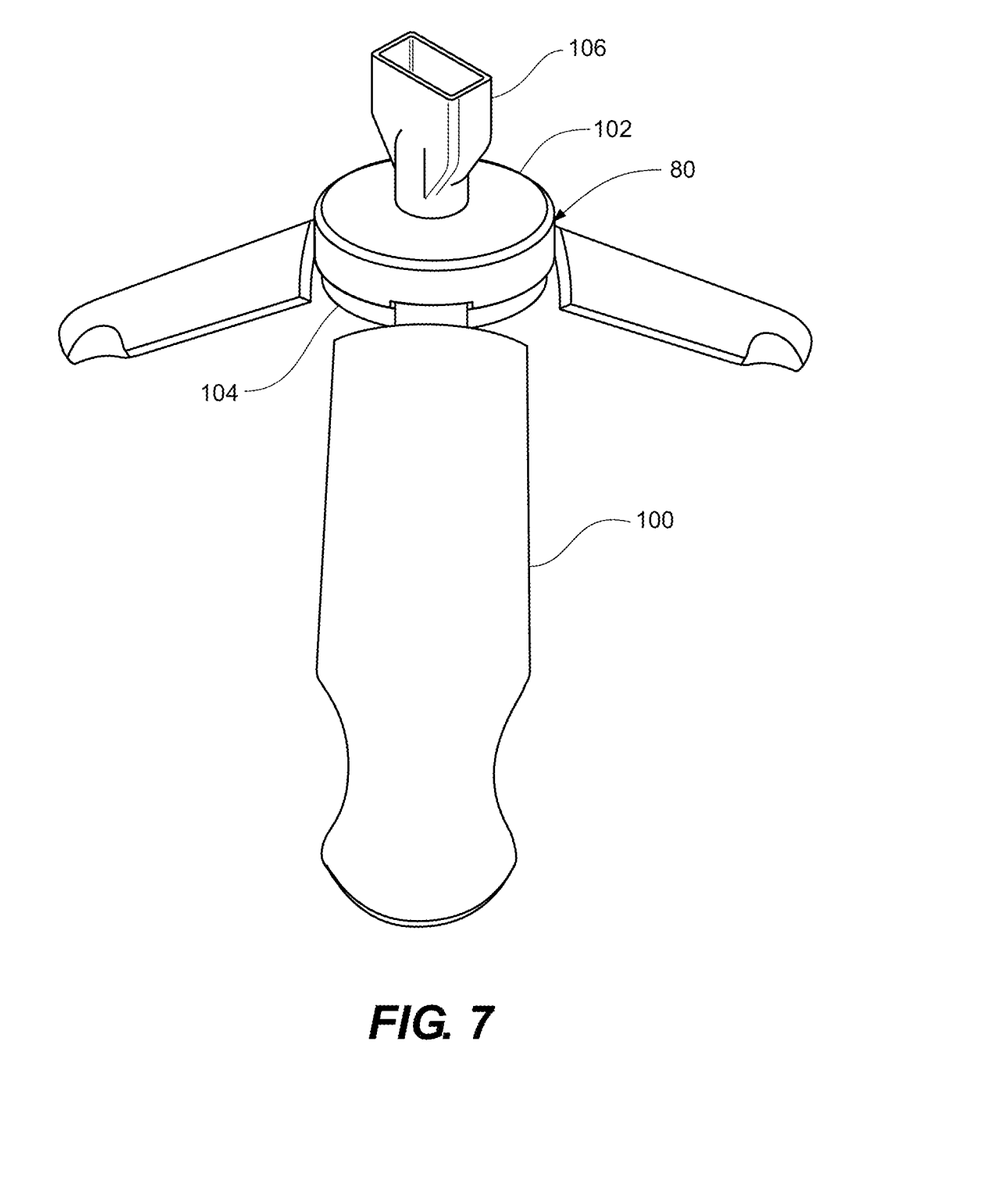
FIG. 7 is a perspective view of a tripod base according to an example embodiment of the invention.

Referring to for example FIGS. 1, 2 and 7, supporting base 28 may include, for example, suction base 78, multi-pod base 80 or magnetic base 82.

Suction base 28, according to an example embodiment, includes cup 84, membrane 86 and coupling pin 88. Cup 84 is sized and adapted to receive membrane 86 therein and presents membrane stem opening 89. Membrane 86 includes suction portion 90 and membrane stem 92. Membrane stem 92, in the depicted embodiment, defines coupling pin aperture 94 therethrough. Membrane stem 92 passes through membrane stem opening 89. Coupling pin aperture 94 is sized and structured to receive coupling pin 88.

Multi-pod base 80, depicted for example in FIG. 7 as an example embodiment includes base bolt (not depicted), base canopy 98 and legs 100. Base bolt (not depicted) extends upwardly from base canopy 98 while legs 100 extend generally downwardly and outwardly from base canopy 98. Base canopy 98 may include upper segment 102 and lower segment 104. Legs 100 may be foldable or fixed and engage base canopy 98. Legs 100 may number three as depicted, or may include more than three legs 100 or even two legs 100.

Base of bolt (not depicted) is structured to threadably couple to light unit dock 106 or to base nut 76 for example.

Referring to FIG. 2, magnetic base 82 includes magnet 108 and base bolt (not depicted).

Figure 8:
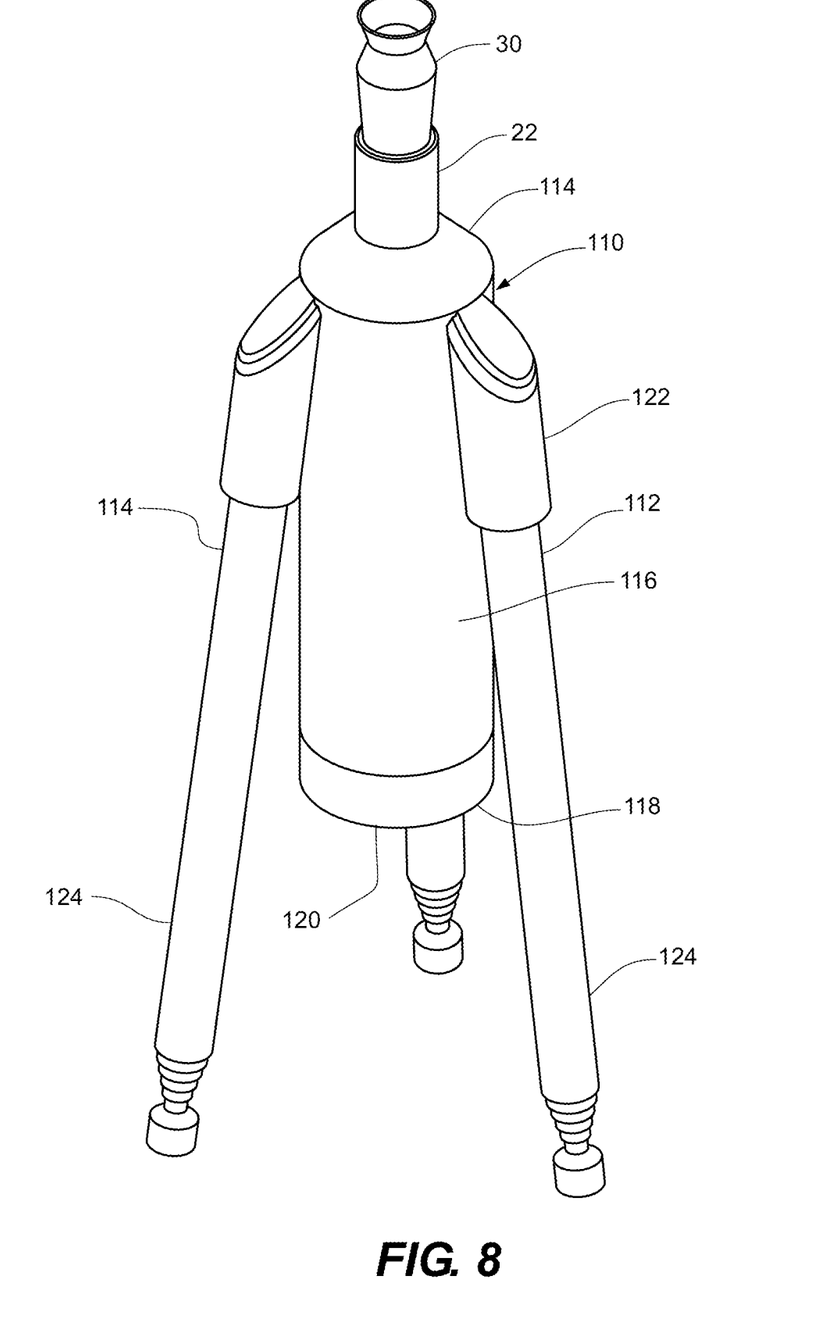
FIG. 8 is a perspective view of a contact lens application aid according to a further example embodiment of the invention.
Figure 9:
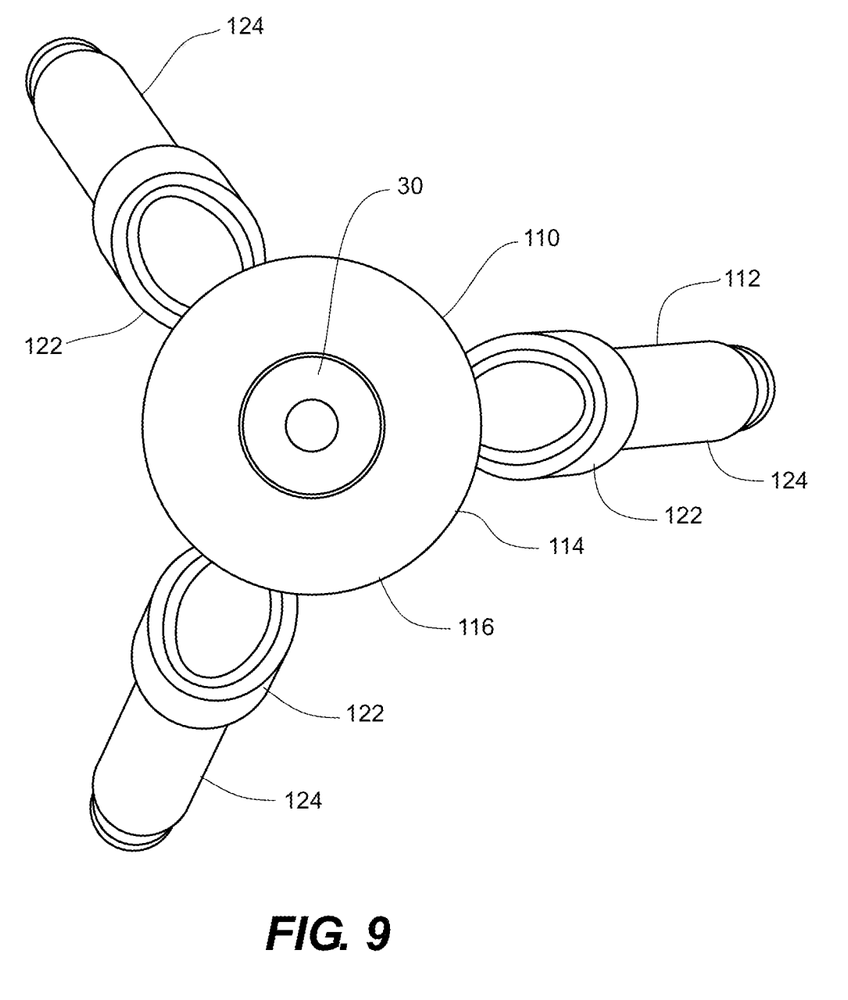
FIG. 9 is a top perspective view of the contact lens application aid as depicted in FIG. 8.

Referring particularly to FIGS. 8 and 9, another embodiment of contact lens application aid 20 includes removable battery light unit 110 with integrated legs 112. Removable battery light unit 110 generally includes lens holder dock 22, and light unit 24 similar to that discussed above. According to this depicted example embodiment, light unit housing 114 is a generally unitary structure and includes battery compartment 116, battery cover 118, switch 120. Cylindrical fins 122 and telescoping legs 124 are coupled thereto light unit housing 114.

In the depicted embodiment, battery cover 118 is removable to provide access to battery compartment 116. Switch 120 is electrically coupled to illuminate or turn off removable battery light unit 110. Cylindrical fins 122 are evenly spaced around light unit housing 114 and are adapted and constructed to receive telescoping legs 124. Telescoping legs 124 telescope in a manner that is known and that is similar to a radio antenna or other telescoping structure.

Lens holder dock 22 is structured and adapted to receive lens holder 30 therein. Lens holder 30 can, for example, include a Vented Scleral Cup manufactured by DMV Corporation. This should not be considered limiting and others lens holders 30 can be utilized.

Figure 11:
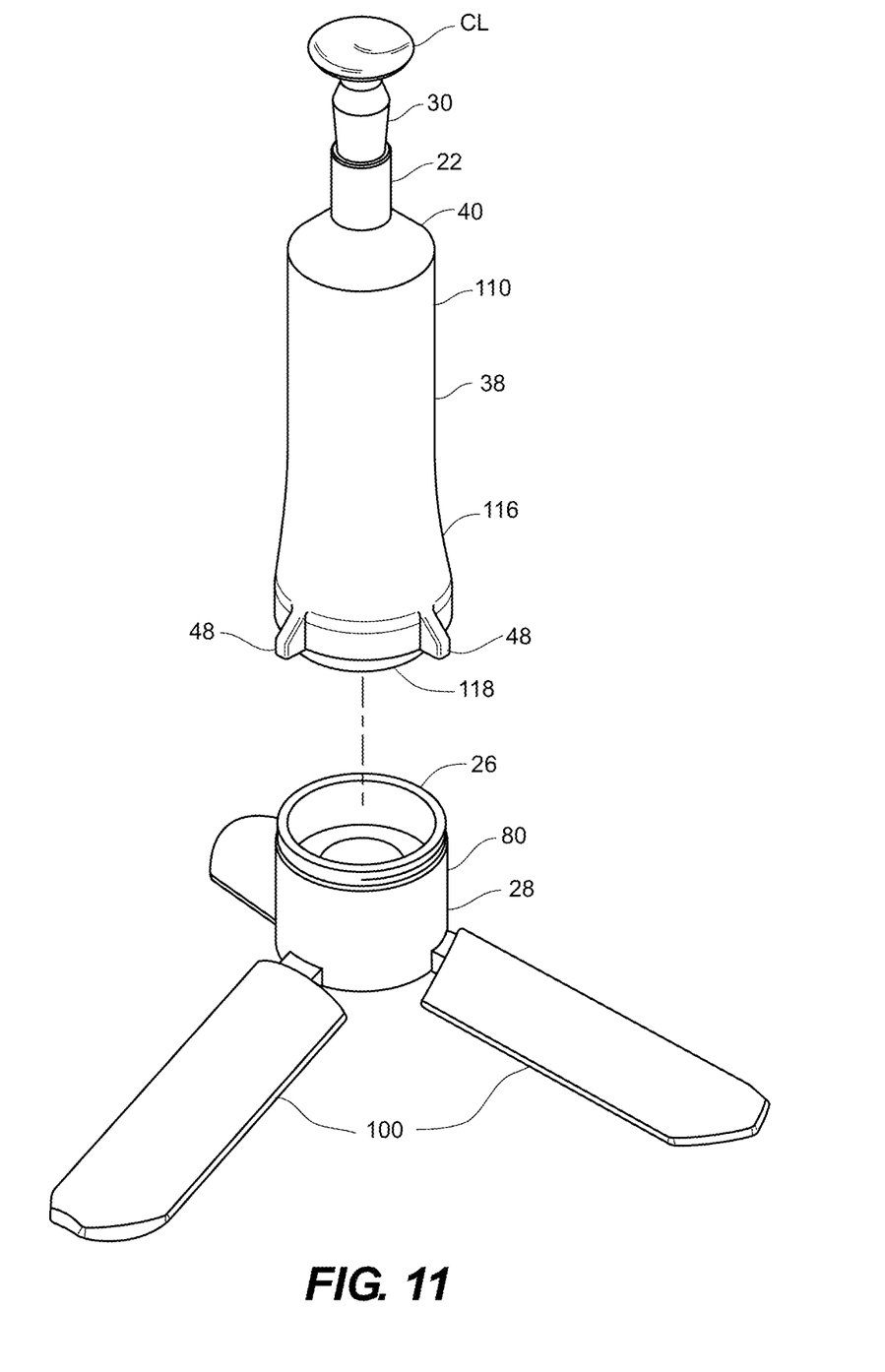
FIG. 11 is a perspective view a further embodiment of the contact lens application aid.
Figure 12:
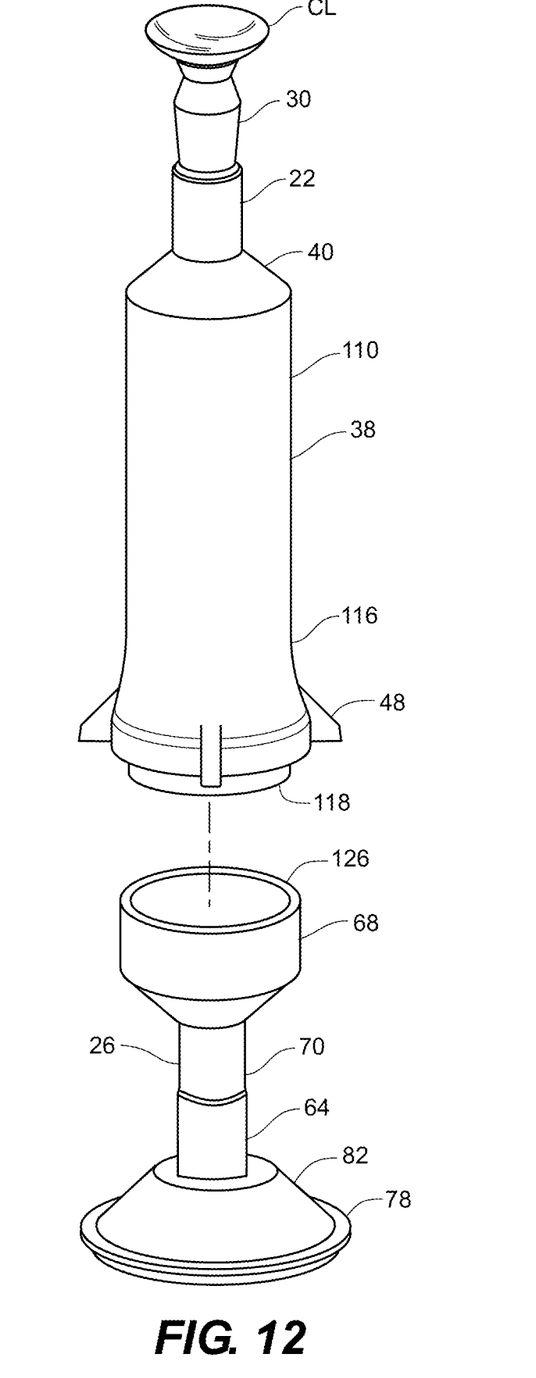
FIG. 12 is a perspective view of yet another embodiment of the contact lens application aid.

Referring now to FIGS. 11 and 12, further embodiments of contact lens application aid are depicted. Here, similar structures are identified by similar reference numerals to those used above.

Referring particularly to FIG. 11, the depicted embodiment includes lens holder dock 22, removable battery light unit 110 supporting member 26 and supporting base 28. Lens holder dock 22 is coupled to frustoconical portion 40 which in turn is coupled to cylindrical portion 38. Cylindrical portion 38 is integrally formed with battery compartment 116 and is removably coupled to battery cover 118. Battery compartment 116 further presents anti-roll fins 48. In the depicted embodiment, contact lens CL rests on lens holder 30.

Supporting base 28 in the depicted embodiment includes multipod base 80. Multipod base 80 includes supporting member 26, supporting base 28 and legs 100. In the depicted embodiment battery cover 118 is sized and shaped to be received into multipod base 80. This may be by a friction fit.

Referring now to FIG. 12, another embodiment of contact lens application a 20 is depicted. Similar to the embodiment depicted in FIG. 11, the depicted embodiment includes lens holder dock 22, removable battery light unit 110, supporting member 26 and supporting base 28. Lens holder dock 22 is coupled to or integrally formed with frustoconical portion 40 which in turn is coupled to cylindrical portion 38. Cylindrical portion 38 is integrally formed with battery compartment 116 is and removably coupled to battery cover 118. Battery compartment 116 further presents anti-roll fins 48. In the depicted embodiment, contact lens CL rests on lens holder 30.

Supporting base 28, in the depicted embodiment, includes suction base 78 or magnetic base 82. In the depicted embodiment, supporting member 26 includes fixed height supporting member 70. As depicted, coupling end 68 is engaged to fixed height supporting number 70 coupled to supporting base 28. In the depicted embodiment, coupling end 68 includes coupling cup 126. Coupling cup 126 is sized and shaped to removably engage to battery cover 118. This may be by a friction fit, for example.

In operation, contact lens application aid 20 is placed on a horizontal surface of convenient height and if adjustable, adjusted in height as desired by the contact lens aid 20 user. Contact lens holder 30 is placed in contact lens holder dock 22 if not already present. Light unit 24 is illuminated by operation of switch 58.

A contact lens CL is then placed on top of lens holder 30 concave side up and the concave side is then filled with a contact lens solution. The user then positions their eye above contact lens holder 30 with contact lens and is able to use both hands to control and open the eyelids to lower the eye to make contact with the contact lens and thus apply the contact lens to the eye.

In the case of embodiments including adjustable height supporting member 72, height may be adjusted by extending or retracting telescoping portions of adjustable height supporting member 72. Similarly in the case of removable battery light unit 110 including integrated legs 112, integrated legs 112 may be extended or retracted in order to adjust height.

In the case of embodiments including suction base 78, suction base 78 may be secured to a smooth surface by operation of base lever 74. Rotation of base lever 74 about coupling pin 88 applies or releases tension on membrane stem 92 thus engaging or disengaging suction portion 90 from the smooth surface.

In the case of embodiments including magnetic base 82, magnet 108 of magnetic base 82 may be applied to or removed from a supporting surface that is ferrous in nature.

In the case of embodiments utilizing multipod base 80, multipod base 80 may be set upon a horizontal supporting surface as desired.

Charging port shroud 36 may be coupled to light unit dock 106 or light unit dock 73 to support light unit 24 as desired.

In the case of light unit 24 including charging port 60, charging port 60 may be coupled to an external power source to charge rechargeable battery 52. If charging port 60 is a USB coupler an external power source may be coupled thereto as known to those skilled in the art.

In the case of removal will battery light unit 110 battery cover 118 may be removed to access battery compartment 116 to remove depleted batteries and insert fresh batteries as needed.

Switch 58 or switch 120 may be actuated as needed to illuminate or turn off light unit 24.

Antiroll fins 48 or in the case of removable battery light unit 110 cylindrical fins 122 mitigate the likelihood of contact lens application a 20 rolling off a horizontal surface.

Base nut 76 may be attached to or removed from base bolt (not depicted) to couple or uncouple components is desired.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A contact lens application aid comprising:
a lens holder dock structured and dimensioned to receive a lens holder;
a first supporting member extending downwardly away from the lens holder dock whereby the lens holder dock is supported at a desired height above a horizontal work surface;
a surface engaging supporting base coupled to the supporting member whereby the supporting member is supported, thereby allowing a user to keep both hands free to manipulate eyelids of the user while applying the contact lens to an eye; and
wherein the supporting base further comprises a multi-pod having a plurality of legs.

2. The contact lens application aid as claimed in claim 1, wherein the first supporting member is adjustable in length thereby enabling adjustment of the desired distance relative to the surface; and
wherein the supporting base is formed by the first supporting member in combination with two additional second and third supporting members that are adjustable in length extending downwardly away from the light unit.

3. The contact lens application aid as claimed in claim 1, wherein the surface engaging supporting base further comprises a suction cup that can be engaged to the surface.

4. The contact lens application aid as claimed in claim 1, wherein the surface engaging supporting base further comprises a magnet that can be engaged to the surface.

5. The contact lens application aid as claimed in claim 1, wherein the supporting member further comprises at a lower end thereof a lever operably coupled to a suction base.

6. The contact lens application aid as claimed in claim 1, wherein the plurality of legs is foldable.

7. A contact lens application aid comprising:
a lens holder dock structured and dimensioned to receive a lens holder;
a first supporting member extending downwardly away from the lens holder dock whereby the lens holder dock is supported at a desired height above a horizontal work surface;
a surface engaging supporting base coupled to the supporting member whereby the supporting member is supported, thereby allowing a user to keep both hands free to manipulate eyelids of the user while applying the contact lens to an eye; and further comprising a light unit optically coupled to the lens holder dock and illuminating the lens holder dock;
wherein the supporting member is removably coupleable to the light unit; and
wherein the light unit further comprises three cylindrical fins structured to receive three telescoping legs that together form the supporting member and the supporting base.

8. The contact lens application aid as claimed in claim 7, wherein the light unit further comprises an upper portion and a lower portion that are releasably coupleable to each other.

9. The contact lens application aid as claimed in claim 8, wherein the light unit further comprises an LED light source, a lens and a switch controlling the LED light source or comprises a phosphorescent or glow-in-the-dark structure.

10. The contact lens application aid as claimed in claim 7, wherein the light unit further comprises a charging port located at a lower end thereof.

11. The contact lens application aid as claimed in claim 10 wherein the charging port located at the lower end thereof is further incorporated into a coupler by which the supporting member can be releasably coupled to the light unit.

12. The contact lens application aid as claimed in claim 7, wherein the light unit further comprises a charging port and charging port shroud which are together structured to engage a light unit dock affixed to an upper end of the supporting member.

13. A method of contact lens application, comprising:
placing a contact lens to be applied on a contact lens holder;
supporting the contact lens holder in a contact lens dock at a distance relative to a supporting surface on a supporting base further comprising a multi-pod having a plurality of legs;
manipulating and controlling eyelids utilizing two hands;
bringing an anterior surface of an eye into contact with the contact lens; and
releasing the eyelids.

14. The method of contact lens application as claimed in claim 13, further comprising:
illuminating the contact lens holder; and
adjusting a distance of the contact lens dock relative to the supporting surface.

15. The method of contact lens application as claimed in claim 14, further comprising:
coupling the contact lens dock and light unit to a supporting member further coupled to a supporting base; and
securing the supporting base to the supporting surface.

16. The method of contact lens application as claimed in claim 15, further comprising:
securing the supporting base to the supporting surface by suction or magnetic force.

17. The method of contact lens application as claimed in claim 14, further comprising:
illuminating contact lens holder by utilizing a light-emitting diode and a lens.

* * * * *